United States Patent
Stewart et al.

(10) Patent No.: US 7,247,602 B2
(45) Date of Patent: Jul. 24, 2007

(54) AGROCHEMICAL FORMULATION AID COMPOSITION AND USES THEREOF

(75) Inventors: James F. Stewart, Kitchener (CA); William G. Brown, Kingsville (CA)

(73) Assignee: Adjuvants Plus Inc., Kingsville, Ontario (CA)

( * ) Notice: Subject to any disclaimer, the term of this patent is extended or adjusted under 35 U.S.C. 154(b) by 718 days.

(21) Appl. No.: 10/630,806

(22) Filed: Jul. 31, 2003

(65) Prior Publication Data

US 2004/0077501 A1   Apr. 22, 2004

Related U.S. Application Data

(63) Continuation-in-part of application No. 10/415,294, filed as application No. PCT/CA01/01508 on Oct. 26, 2001, now Pat. No. 6,936,572.

(30) Foreign Application Priority Data

Oct. 26, 2000   (CA)   ................................. 2324677

(51) Int. Cl.
*A01N 25/00*   (2006.01)

(52) U.S. Cl. .................................................. 504/116.1

(58) Field of Classification Search .............. 504/116.1
See application file for complete search history.

(56) References Cited

U.S. PATENT DOCUMENTS

| | | | |
|---|---|---|---|
| 4,368,207 A | 1/1983 | Lover et al. | ................ 514/724 |
| 5,238,905 A | 8/1993 | Atwater | |
| 5,783,202 A | 7/1998 | Tomlinson et al. | ......... 424/405 |
| 5,849,264 A | 12/1998 | Bassam et al. | |
| 5,877,112 A * | 3/1999 | Roberts et al. | ............. 504/206 |
| 6,165,939 A * | 12/2000 | Agbaje et al. | .............. 504/105 |

FOREIGN PATENT DOCUMENTS

| | | |
|---|---|---|
| EP | 0 057 035 A | 8/1982 |
| EP | 0 617 894 A | 10/1994 |
| GB | 1 576 228 A | 10/1980 |
| WO | WO 93/14637 | 8/1993 |

* cited by examiner

*Primary Examiner*—Alton Pryor
(74) *Attorney, Agent, or Firm*—David Conn; Borden Ladner Gervais LLP

(57) ABSTRACT

There is provided an agrochemical formulation aid composition for use with technical grade, manufacturing concentrates or pre-formulated Agricultural Chemicals/pesticides, fertilizers and the like comprising about 1 to 99 parts by weight of monocarbamide dihydrogen sulphate and 50 to 10 parts by weight of a blend, said blend comprising: 1-99% by weight of a phosphate ester blend; 99-1% by weight of a tallow amine ethoxylate; 0-5% by weight of a fatty acid methyl ester; 0-0.5% by weight of a free fatty acid blend; 0-0.5% by weight of 2N-octanol; 0-1% by weight of oleyl-cetyl alcohol; 0-0.1% by weight of N-butanol; 0-1.5% by weight of polyethylene glycol; and balance, if any, of water. Also provided are methods of preparing the formulation aid composition on site by mixing various components and methods of preparing sprayable and bioactive agrochemical systems using the formulation aid and non-formulated or formulated agrochemicals. Also provided are uses of the formulation aid in preparing sprayable and bioactive agrochemical systems for controlling pests.

5 Claims, No Drawings

AGROCHEMICAL FORMULATION AID COMPOSITION AND USES THEREOF

CROSS-REFERENCE TO RELATED APPLICATIONS

The present application is a continuation-in-part of U.S. Ser. No. 10/415,294 (unofficial number) filed on Oct. 26, 2001 as PCT/CA01/01508, the entire contents of which are incorporated by reference.

FIELD OF THE INVENTION

This invention relates to agrochemical formulation aid compositions, their uses, and processes of preparing agrochemical systems of non-formulated and formulated agrochemicals using the formulation aid compositions to obtain improved sprayability and bioactivity.

BACKGROUND OF THE INVENTION

Agriculture chemicals (agrochemicals) such as pesticides, fertilizers and the like including insecticides, fungicides, rodenticides, and herbicides are materials that provide control of agricultural pests including insects, pathogens, rodents, and weeds. In order for many agrochemicals to be used as a means of controlling pests, these agrochemicals have to be incorporated into an agriculturally acceptable carrier. Generally, the agrochemical is modified into a soluble ester, amine salt, or dissolved in a solvent system and added to this are products to create an agriculturally acceptable spray solution or suspension with water as a carrier. The carrier systems may also include several other components.

Agricultural adjuvants are materials that modify the performance of an agrochemical and may also improve the physical properties of an agricultural formulation. For example, an activator adjuvant increases the biological efficacy of an agrochemical. Also, fertilizers such as urea or diammonium phosphate are frequently used as adjuvants or are used with other adjuvants to improve the efficacy of agrochemical formulations. A compatibility agent prevents the chemical interaction of two or more agrochemical components in a mixture. It could also improve the homogeneity of additional components such as fertilizers with other agrochemicals in a mixture. A wetting agent or spreading agent increases the surface area covered by a given volume of a spray mixture.

Herein, the term "non-formulated agrochemical" includes pesticides that are sold as technical acids or as technical acid grade products. The terms "formulated agrochemical" and "pre-formulated agrochemical" have been used interchangeably and includes pesticides that are sold as ester, amine salts, or in a solvent.

Currently, most agrochemicals have to be pre-formulated e.g., as emulsifiable concentrates, flowables, soluble powders, or soluble liquids to enable their application e.g., by spraying, on a crop and to make them bioactive for a targeted substrate e.g., a pest. However, the formulated products sold in the form of amines or esters have higher vapor pressure. Therefore, they have a tendency to move off the site of application to trespass and damage adjacent crops and horticultural plantings. The use of solvents such as xylene, isobutanol, and dimethyl amine in formulated products presents the problem of toxicity, odor, and potential explosiveness to the user and neighbors.

However, all prior art adjuvants lack versatility or they often limit the form in which an agrochemical may be pre-formulated as a manufactured product. Further, a pre-formulated manufactured product when shipped must be stored under appropriate environmental conditions to ensure that the agrochemical is not adversely affected in terms of its activity and to ensure that the formulation remains stable. For example, agrochemical formulations often include emulsions in which water is one of the phases. These agrochemical formulations must be stored under conditions that protect the emulsion from freezing. Further, it should be noted that different levels of adjuvants are used with a given level of the pesticide for different crop applications, different stages of crop growth, different weather or climate conditions, and target species. Pre-formulating a given agrochemical to meet such diverse needs thus requires the construction of formulation facilities that use costly energy and create toxic wastes as byproducts such as aromatic petrochemicals. Further, the pre-formulated agrochemical products often require the addition of an adjuvant or water conditioner to provide enhanced bioactivity and/or spray applicability.

The present invention provides agrochemical formulation-aid compositions, which overcome disadvantages exhibited by the prior art. The present invention provides agrochemical formulation-aid compositions which permit on-site formulation of an agrochemical, a mixture of agrochemicals, or pre-formulated products prior to use. It thus becomes unnecessary to first formulate the active ingredient to render it bioactive and sprayable. It also significantly ameliorates any storage problems since the present invention makes it possible to formulate the agrochemical mixture as needed and just prior to its use. In most applications, the only equipment required to use the agrochemical formulation aid of the present invention is a means to measure quantities reasonably accurately, and an adequately powerful stirrer. Thus, both the equipment and energy requirements for formulation are significantly reduced, thereby reducing environmental and toxic byproducts in comparison with the known manufacturing processes used to produce both pre-formulated products, and the materials used in them in addition to the agrochemicals. The agrochemical formulation aid of the present invention is a free flowing material that disperses completely and rapidly in water. The agrochemical formulation aids of the present invention also improve the uptake and performance of pre-formulated agrochemicals, such improvement has not been provided hitherto by a range of other adjuvants. Technical acids of herbicides tend have lower vapor pressure when solubilized in a carrier. The formulation aid of the present invention is non-toxic and odorless unlike the solvents used in formulated products.

SUMMARY OF THE INVENTION

It is an object of the present invention to provide an agrochemical formulation aid composition for formulating an agrochemical, a mixture of agrochemicals, or pre-formulated products prior to use in a bioactive and sprayable form. The agrochemical formulation aid may be used on-site prior to use.

It is another object of the present invention to provide an agrochemical formulation aid composition for formulating non-formulated pesticides and pre-formulated pesticides.

It is yet another object of the present invention to provide a formulation aid that is a free flowing material that disperses completely and rapidly in water.

It is yet another object of the present invention to provide a formulation aid that improves the bioactivity of even pre-formulated agrochemicals.

It is yet another object of the present invention to provide a formulation aid that is easy to store and requires simple equipment for measuring quantities reasonably accurately, a mixing-container and a stirrer.

It is yet another object of the present invention to provide formulation aid that has reduced energy requirements and reduced environmental and toxic byproducts.

It is yet another object of the present invention to provide a formulation aid composition that can be used for different crop applications, different stages of crop growth, different weather or climate conditions, and target species.

It is yet another object of the present invention to provide a formulation aid composition that is applicable at lower vapor pressure and has no odor problems.

It is yet another object of the present invention to provide a means to further improve the bioactivity of pesticides by adding a fertilizer to the formulation aid.

Accordingly, there is provided an agrochemical formulation aid composition comprising about 1 to 99 parts by weight of monocarbamide dihydrogen sulphate and 50 to 1 parts by weight of a blend, said blend comprising: 1-99% by weight of a phosphate ester blend; 99-1% by weight of a tallow amine ethoxylate; 0-25% by weight of a fatty acid methyl ester; 0-5% by weight of a free fatty acid blend: 0-10% by weight of a linear alcohol blend; 0-1% by weight of oleyl-cetyl alcohol; 0-10% by weight of polyethylene glycol; and balance, if any, of water. Preferably, the agrochemical formulation aid composition comprises about 1 to 99 parts by weight of monocarbamide dihydrogen sulphate and 50 to 1 parts by weight of a blend, said blend comprising: 1-99% by weight of a phosphate ester blend; 99-1% by weight of a tallow amine ethoxylate; 0-25% by weight of a fatty acid methyl ester; 0-5% by weight of a free fatty acid blend; 0-0.5% by weight of 2N-octanol; 0-1% by weight of oleyl-cetyl alcohol; 0-1% by weight of N-butanol; 0-10% by weight of polyethylene glycol; and balance, if any, of water. Particularly preferred is a formulation in which the blend comprises: about 3-5% by weight of a fatly acid methyl ester; about 0-0.5% by weight free fatty acid blend; about 0-0.5% by weight 2N-octanol; about 0-1% by weight of oleyl-cetyl alcohol; from about 0-0.1% by weight N-butanol; from about 3-10% by weight of a phosphate ester blend of alkyl(aryl) ethoxylate phosphate ester; from about 3-12% by weight tallow amine ethoxylate: and from about 0.5 to 1.5% by weight polyethylene glycol. A particular formulation comprises about 85% by weight of monocarbamide dihydrogen sulphate and about 15% by weight of said blend, said blend comprising: 31% phosphate ester blend; 21.5% by weight tallow amine ethoxylate, 20.7% methyl soyate, 7.2% polyethylene glycol, 5.8% linear alcohol blend, 1.9% tall oil fatty acid, 0.9% by weight butanol, and 11% water. A particular group of compositions of the invention comprises about 85% by weight of monocarbamide dihydrogen sulphate and about 15% by weight of said blend, said blend comprising about 1 to 99% (particularly 25-75%) by weight of a phosphate ester blend of alkyl(aryl) ethoxylate phosphate esters and about 99 to 1% (particularly 75-25%) by weight of a tallow amine ethoxylate. Also provided are methods of preparing the formulation aid composition on site by mixing various components and methods of preparing sprayable and bioactive agrochemical system using the formulation aid and non-formulated and/or formulated agrochemicals. Also provided are uses of the formulation aid in preparing sprayable and bioactive agrochemical systems for controlling pests.

DETAILED DESCRIPTION OF THE PREFERRED EMBODIMENTS

The present invention relates to agrochemical formulation aid compositions, their uses, and methods of preparations. The invention also relates to methods of preparing agrochemical systems of non-formulated and pre-formulated agrochemicals using the formulation aid compositions to obtain improved tank-spray capability and bioactivity.

In an embodiment, the formulation aid composition comprises effective amounts of adjuvants, dispersants, emulsifiers, penetrants, surfactants, distillates, water conditioners, and fertilizers for improved bioactivity and sprayability.

In a preferred embodiment the adjuvants, dispersants, emulsifiers, penetrants, surfactants, distillates, water conditioners, and fertilizers for improved bioactivity and spray applicability are selected from mineral oil paraffinic distillate; 2N-octanol; oleyl-cetyl alcohol; polyoxyethylene (2) oleylether; polyoxyethylene (8) nonylphenolethin; sodium lauryl sulphate; fatty alcohol alkoxylate; terpenes, preferably from a plant source; diammonium phosphate; tetrasodium ethylene diamine tetracetate; and cab-o-sil. The diammonium phosphate may be replaced with an alternative nitrogen-containing nutrient such as ammonia, ammonium nitrate, or ammonium sulphate.

More preferably, the formulation aid comprises from about 135 to about 165 parts by weight mineral oil paraffinic distillate; from about 23 to about 29 parts by weight 2N-octanol; from about 42 to about 52 parts by weight oleyl-cetyl alcohol; from about 46 to about 56 parts by weight polyoxyethylene (2) oleylether; from about 9 to about 11 parts by weight polyoxyethylene (8) nonylphenolethin; from about 1.2 to about 1.4 parts by weight sodium lauryl sulphate; from about 36 to about 43 parts by weight fatty alcohol alkoxylate; from about 7.5 to about 9.5 parts by weight terpenes, preferably from a plant source; from about 2.2 to about 2.8% w/v tetrasodium ethylene diamine tetracetate; and from about 8 to about 22 parts by weight of cab-o-sil for improved bioactivity and sprayability. From about 610 to about 670 parts by weight of a mixture containing from about 0.8 to about 1.2 parts by weight of diammonium phosphate in 2.7 to 3.3 parts by weight water may also be added. The diammonium phosphate may be replaced with an alternative nitrogen-containing nutrient such as ammonia, ammonium nitrate, or ammonium sulphate. The amount of polyoxyethylene (8) nonylphenolethin may be selected from about 3 to about 60 parts by weight. In an alternate embodiment, the formulation aid composition may further comprise of from about 5 to about 15 parts by weight of methyl alcohol.

Particularly preferably, the formulation aid comprises from about 143 to about 158 parts by weight mineral oil paraffinic distillate; from about 21.5 to about 27.5 parts by weight 2N-octanol; from about 44 to about 49 parts by weight oleyl-cetyl alcohol; from about 48 to about 53 parts by weight polyoxyethylene (2) oleylether; from about 9.5 to about 10.5 parts by weight polyoxyethylene (8) nonylphenolethin; from about 1.2 to about 1.4 parts by weight sodium lauryl sulphate; from about 38 to about 42 parts by weight fatty alcohol alkoxylate; from about 8 to about 9 parts by weight terpenes, preferably from a plant source; from about 2.35 to about 2.65% w/v tetrasodium ethylene diamine tetracetate; from about 9 to about 21 parts by weight of cab-o-sil for improved bioactivity and sprayability. From about 636 to about 704 parts by weight of a mixture containing from about 0.9 to about 1.1 parts by weight of diammonium phosphate in 2.85 to 3.15 parts by weight water may be added further. The diammonium phosphate may be replaced with an alternative nitrogen-containing nutrient such as ammonia, ammonium nitrate, or ammonium sulphate.

In a specially preferred embodiment, the formulation aid comprises about 150 parts by weight mineral oil paraffinic distillate; about 26 parts by weight 2N-octanol; about 47.2 parts by weight oleyl-cetyl alcohol; about 50.2 parts by weight polyoxyethylene (2) oleylether; about 10 parts by weight polyoxyethylene (8) nonylphenolethin; 1.0 parts by weight sodium lauryl sulphate; about 39.4 parts by weight fatty alcohol alkoxylate; about 8.6 parts by weight terpenes, preferably from a plant source; about 2.5% w/v tetrasodium ethylene diamine tetracetate; and from about 10 to about 20 parts by weight of cab-o-sil for improved bioactivity and sprayability. About 667 parts by weight of a mixture containing about 1 part by weight of diammonium phosphate in 3 parts by weight water may be added further. The diammonium phosphate may be replaced with an alternative nitrogen-containing nutrient such as ammonia, ammonium nitrate, or ammonium sulphate.

The above described formulation aids of the present invention were prepared by a three-part process comprising a step A followed by steps B and C, wherein step A comprises the following sub steps: placing from about 135 to about 165 parts by weight mineral oil paraffinic distillate in a suitable container with stirring means; adding from about 23 to about 29 parts by weight 2N-octanol and mixing; adding from about 42 to about 52 parts by weight oleyl-cetyl alcohol to the mixture and continuing mixing for up to about 8 minutes at a temperature of about 25° C. until a homogenous mixture is obtained; adding from about 1.2 to about 1.4 parts by weight sodium lauryl sulphate and mixing it slowly until it dissolved; adding from about 46 to about 56 parts by weight polyoxyethylene (2) oleylether slowly and mixing it until dissolved; adding from about 9 to about 11 parts by weight polyoxyethylene (8) nonylphenolethin slowly and mixing it until dissolved; adding from about 36 to about 43 parts by weight fatty alcohol alkoxylate and mixing until it dissolved; adding from about 7.5 to about 9.5 parts by weight terpenes, preferably from a plant source, and mixing until the resulting mixture is homogenous. The range for polyoxyethylene (8) nonylphenolethin may be selected from about 3 to about 60 parts by weight for preparing the formulation aid.

The preparation of the formulation aid may additionally comprise of adding from about 5 to about 15 parts by weight of methyl alcohol to the mixture and mixing.

Step B comprises adding from about 0.8 to about 1.2 parts by weight of diammonium phosphate to 2.7 to 3.3 parts by weight water at a temperature of about 60° C. and mixing until it dissolved; adding form about 2.2 to about 2.8% w/v tetrasodium ethylene diamine tetracetate to the mixture; and adding from about 8 to about 22 parts by weight of cab-o-sil and mixing until it dispersed;

Step C comprises combining from about 610 to about 670 parts by weight of the product of step B to the product of step A and continuing mixing until a stable uniform homogenous blend is obtained.

In another embodiment the adjuvants, dispersants, emulsifiers, penetrants, surfactants, distillates, water conditioners, and fertilizers for improved bioactivity and sprayability may be selected from aromatic hydrocarbon distillate, 2N-octanol, oleyl-cetyl alcohol, polyoxythylene (8) nonylphenolethin, polyoxyalkylated fatty alcohol, and ethoxylated tallow amine blend.

Preferably, the formulation aid of present invention comprises from about 10 to 40% by weight aromatic hydrocarbon distillate, from about 3 to 6% by weight of 2N-octanol, from about 5 to 10% by weight oleyl-cetyl alcohol, from about 0 to about 4% by weight of polyoxyethylene (8) nonylphenolethin, from about 25 to 35% by weight of polyoxyalkylated fatty alcohol, and from about 20% to 35% by weight of ethoxylated tallow amine blend.

In a preferred embodiment, the formulation aid comprises about 21.5% by weight aromatic hydrocarbon distillate, about 3.1% by weight 2N-octanol, about 5.7% by weight oleyl-cetyl alcohol, about 3.1% by weight polyoxyethylene (8) nonylphenolethin, about 33.3% by weight polyoxyalkylated fatty alcohol, and from about 33.3% by weight ethoxylated tallow amine blend.

In a more preferred embodiment, the formulation aid comprises about 23.6% by weight aromatic hydrocarbon distillate, about 3.5% by weight 2N-octanol, about 6.3% by weight oleyl-cetyl alcohol, about 33.3% by weight polyoxyalkylated fatty alcohol, and from about 33.3% by weight ethoxylated tallow amine blend.

In an especially preferred embodiment, the formulation aid comprises about 35.4% by weight aromatic hydrocarbon distillate, about 5.2% by weight 2N-octanol, about 9.4% by weight oleyl-cetyl alcohol, about 25.0% by weight polyoxyalkylated fatty alcohol, and about 25.0% weight ethoxylated tallow amine blend.

The above described formulation aids of the present invention can be prepared by a one-part process comprising the following steps: placing from about 10 to 40% by weight aromatic hydrocarbon distillate in a suitable container containing stirring means; adding from about 3 to 6% by weight of 2N-octanol to the mixture; adding from about 5 to 10% by weight oleyl-cetyl alcohol to the mixture and continuing mixing for up to 8 minutes at a temperature of about 25° until a homogenous mixture is obtained; adding from 0 to about 4% by weight of polyoxyethylene (8) nonylphenolethin slowly and mixing until it dissolved; adding from about 25 to 35% by weight of polyoxyalkylated fatty alcohol and mixing until it dissolved; and adding from about 20% to 35% by weight of ethoxylated tallow amine blend and agitating until the resulting mixture is homogenous.

In yet another embodiment the adjuvants, dispersants, emulsifiers, penetrants, surfactants, distillates, water conditioners, and fertilizers for improved bioactivity and spray applicability are selected from mineral oil paraffinic distillate, aromatic hydrocarbon, surfactant blend, 2N-octanol, oleyl-cetyl alcohol, polyoxyalkylated fatty alcohol, and ethoxylated tallow amine blend.

In a preferred embodiment, the formulation aid of present invention contained about 6 to 8% by weight of mineral oil paraffinic distillate, from about 10 to 15% by weight aromatic hydrocarbon distillate, from about 5 to 7% by weight of surfactant blend, from about 1 to 3% by weight of 2N-octanol, from about 2 to 5% by weight of oleyl-cetyl alcohol, from about 25 to 35% by weight of polyoxyalkylated fatty alcohol, and from about 25-35% by weight of ethoxylated tallow amine blend.

In a especially preferred embodiment, the formulation aid of present invention comprises about 6.7% by weight of mineral oil paraffinic distillate; about 14.9% by weight of aromatic hydrocarbon distillate; about 5.7% by weight of surfactant blend; about 2.2% by weight of 2N-octanol; about 3.9% by weight of oleyl-cetyl alcohol; about 33.3% by weight of polyoxyalkylated fatty alcohol; and about 33.3% by weight of ethoxylated tallow amine blend for improved bioactivity and sprayability.

In yet another embodiment the adjuvants, dispersants, emulsifiers, penetrants, surfactants, distillates, water conditioners, and fertilizers for improved bioactivity and sprayability may be selected from fatty acid methyl ester, preferably from a vegetable source; (C18) free fatty acid blend; oleyl-cetyl alcohol; N-butanol; polyoxyalkylated fatty alcohol; and ethoxylated tallow amine blend.

In a preferred embodiment, the formulation aid of present invention contained from about 20-25% by weight of a fatty acid methyl ester, preferably from a vegetable source; from about 0.1-3% by weight of (C18) free fatty acid blend; from about 0.5 to 3% by weight of 2N-octanol, from about 1-6 by weight of oleyl-cetyl alcohol; from about 0.1 to 1% by weight of N-butanol; from about 25 to 35% by weight of polyoxyalkylated fatty alcohol; and from about 25 to 35% by weight of ethoxylated tallow amine surfactant blend for improved bioactivity and sprayability.

In a especially preferred embodiment, the formulation aid of present invention comprises about 24.4% by weight of vegetable fatty acid methyl ester, about 2% by weight of (C18) free fatty acid blend; about 2% by weight of 2N-octanol, about 4% by weight of oleyl-cetyl alcohol; about 1% by weight of N-butanol; about 33.3% by weight of polyoxyalkylated fatty alcohol; and about 33.3% by weight of ethoxylated tallow amine surfactant blend for improved bioactivity and sprayability.

The above described formulation aids of the present invention can be prepared by a one-part process comprising the following steps: placing from about 20-25% by weight of fatty acid methyl ester, preferably from a vegetable source in a suitable container with stirring apparatus and mixing it; adding from about 0.1-3% by weight of (C18) free fatty acid blend to the mixture; adding from about 2% by weight of 2N-octanol and mixing; adding from about 1-6 by weight of oleyl-cetyl alcohol to the mixture; adding from about 0.1 to 1% by weight of N-butanol to the mixture; adding from about 25 to 35% by weight of polyoxyalkylated fatty alcohol to the mixture and mixing until it dissolved; and adding from about 25 to 35% by weight of ethoxylated tallow amine surfactant blend and mixing it until the resulting mixture is homogenous.

In yet another embodiment, the formulation aid of present invention comprises about 27 parts by weight water; about 2 parts by weight free fatty acid blend; about 2 parts by weight 2N-octanol; about 4 parts by weight oleyl-cetyl alcohol, about 1 part by weight N-butanol; about 33.3 parts by weight polyoxyalkylated fatty alcohol; and about 33.3 parts by weight ethoxylated tallow amine surfactant blend.

The agrochemical formulation aids described above can be stored under reasonable conditions, such as a temperature of below about 35° C. Although some of the formulation aids contain water, freezing does not damage the formulation aid. If minor separation of phases does occur in the formulation aid, the agrochemical formulation aid can be readily re-dispersed to become homogenous by mixing. Some formulation aids do not contain water and are fully stable with prolonged shelf life.

The formulation aids described above have been used to prepare sprayable and bioactive mixtures with a number of non-formulated i.e., technical acids or formulated herbicides alone or in combination. These sprayable and bioactive mixtures were sprayed on a number of plant species under variety of conditions in a variety of locations to show their effectiveness. Percentage control of weeds or percentage injury to specific crops was recorded as a measure of their effectiveness.

The invention will be illustrated with reference to the following examples.

EXAMPLE 1

Preparation of Sprayable and Bioactive Agrochemical and Formulation Aid Mixture Prior to any preparation all spray-mixing and application equipment were cleaned thoroughly by observing cleaning directions provided on the agrochemical labeling and accompanying materials provided by the maker. Half of the required water was placed in a spray tank. A required amount of the formulation aid was added in the spray tank for the required rate of glyphosate application as indicated in Table 1. A required amount of herbicide e.g., glyphosate technical acid active ingredient or product, as indicated in Table 1, was added to the spray tank. Mixing was continued and remainder of the water was added to the spray tank. Mixing was continued for another 5-10 minutes. The ready to use herbicide and formulation aid mixture was applied by spraying at the required rate.

Table 1 shows the amounts of glyphosate technical acid (N-phosphonomethylglycine, 95-99.9%) active ingredient or product and formulation aid required to prepare sprayable and bioactive glyphosate and formulation aid mixture.

EXAMPLE 2

Control of Broad-spectrum Weeds by Using Formulation Aid with Non-formulated Glyphosate Technical Acid Table 2 shows control of broad-spectrum weeds at commercial levels by using formulation aid of the present invention with a non-formulated herbicide, glyphosate technical acid at various rates. The results shown in Table 2 were obtained by applying glyphosate technical acid (95%) and the formulation aid mixture to 10 fields infected with various annual and perennial weeds (indicated in Table 2). The experiments were conducted between the period of September 1998 to August 2000.

Hundred percent weed control was obtained 21 days after treatment (DAT) at a spray volume of 100 l/ha at different rates. No weed control was observed when formulation aid was replaced with water. Additional supporting efficacy was independently collected on weeds such as giant foxtail, yellow foxtail, velvet leaf, smart weeds, ragweed species, venice mallow, entire leaf morning glory from research trials (small plot and grower trials) in various countries. The results demonstrate the utility of the formulation aid of the present invention in preparing a sprayable and bioactive mixture of technical acid of a herbicide for controlling weeds.

The formulation aid tested in this example contained about 21.5% by weight aromatic hydrocarbon distillate, about 3.1% by weight 2N-octanol, about 5.7% by weight oleyl-cetyl alcohol, about 3.1% by weight polyoxyethylene (8) nonylphenolethin, about 33.3% by weight polyoxyalkylated fatty alcohol, and about 33.3% by weight ethoxylated tallow amine blend.

EXAMPLE 3

Control of Broad-spectrum Weeds by Using Formulation Aid with Non-formulated Dicamba Technical Acid Table 3 shows control of broad-spectrum weeds at commercial levels by using formulation aid of the present invention with another non-formulated herbicide, Dicamba technical acid at various rates. The results shown in Table 3 were obtained by applying the mixture of dicamba technical acid (87%) and the formulation aid to two fields infected with various annual and perennial weeds (indicated in Table 3). The experiments were conducted between the period of September 1998 to August 2000.

Hundred percent weed control was obtained 21 days after treatment (DAT) at a spray volume of 200 l/ha at different rates. No weed control was observed when formulation aid was replaced with water. Similar results were obtained independently on weeds such as giant foxtail, yellow foxtail, Velvetleaf, Smartweeds, ragweed species, venice mallow, entire leaf morning glory from research trials (small plot and grower trials) in various countries. The results demonstrate the utility of the formulation aid of the present invention in preparing sprayable and bioactive of dicamba technical acid in controlling weeds.

The formulation aid used in this example contained about 150 parts by weight mineral oil paraffinic distillate; about 26 parts by weight 2N-octanol; about 47.2 parts by weight oleyl-cetyl alcohol; about 50.8 parts by weight polyoxyethylene (2) oleylether; about 10 parts by weight polyoxyethylene (8) nonylphenolethin; 1.3 parts by weight sodium lauryl sulphate; about 39.4 parts by weight fatty alcohol alkoxylate; about 8.6 parts by weight plant terpenes; about 667 parts by weight of a mixture containing about 1 part by weight of diammonium phosphate in 3 parts by weight water about 2.5% w/v tetrasodium ethylene diamine tetracetate (EDTA); and from about 10 to about 20 parts by weight of cab-o-sil for improved bioactivity and sprayability.

Table 4 shows the amounts of dicamba technical acid (3,6-dichloro-2methoxybenozic acid, 88-95%) and formulation aid required to prepare a sprayable and bioactive mixture.

EXAMPLE 4

Effective Weed Control with Sprayable and Bioactive Mixture of Formulation Aid and Glyphosate Technical Acid Table 5 shows the effectiveness of using a mixture of glyphosate technical acid 95% or glyphosate 97.3% wet cake isopropyl amine (IPA) technical acid and the formulation aid in comparison to Roundup Transorb, a pre-formulated herbicide preparation, 27 days after treatment. The plots (2×10 meters) were treated with a precision plot spray system and applied with 100 l/ha water at 220 kPa through a four nozzle (50 cm spacing) hand-held (2 meter) boom using TeeJet flat fan 8002 nozzles. The application was done in the summer of 1999. The results from 4 replicates were not significantly different among different treatments after 27 days. All combinations performed equally well on the four weed species and provided excellent weed control at the rates used. The results indicate that a herbicide mixture prepared with the formulation aid of the present invention performed equally well as compared to a pre-formulated herbicide.

The agrochemical formulation aid tested in the above example with glyphosate technical acid contained about 150 parts by weight mineral oil paraffinic distillate; from about 26 parts by weight 2N-octanol; from about 48 parts by weight oleyl-cetyl alcohol; about 50 parts by weight polyoxyethylene (2) oleylether; about 5 parts by weight polyoxyethylene (8) nonylphenolethin; about 1.3 parts by weight sodium lauryl sulphate; about 40 parts by weight fatty alcohol alkoxylate; about 8 parts by weight plant terpenes; about 667 parts by weight of diammonium phosphate in three parts by weight water. In an alternate embodiment, diammonium phosphate was replaced with an alternative nitrogen-containing nutrient such as ammonium sulphate or ammonium nitrate.

EXAMPLE 5

Control of Pre-plant Vegetation Using a Sprayable and Bioactive Mixture of Glyphosate Technical Acid and Formulation Aid Table 6 shows pre-plant vegetation control when glyphosate technical acid 95% was applied with one of the formulation aids of the present invention in comparison to Roundup Ultra, a pre-formulated glyphosate herbicide. The application was done in Summer of 2000. Table 6 shows percent control 14 days after treatment (DAT). Application was made with a research plot sprayer with 42 lbs pressure and 20 gallons of water through DG 11002 nozzles to plots measuring 6.67 ft×20 ft.

As shown in Table 6, formulation aid and formulation aid with ammonium sulphate controlled all plant species tested with slight variations. The formulation aid and glyphosate technical acid 95% proved slightly less effective on Velvetleaf but addition of ammonium sulphate improved Velvetleaf control in comparison to Roundup Ultra. The formulation aid and Glyphosate technical acid 95% with or without ammonium sulphate proved superior for control of Smartweed in comparison to Roundup Ultra.

The agrochemical formulation aid tested in the above example with glyphosate technical acid contained about 150 parts by weight mineral oil paraffinic distillate; from about 26 parts by weight 2N-octanol; from about 48 parts by weight oleyl-cetyl alcohol; about 50 parts by weight polyoxyethylene (2) oleylether; about 50 parts by weight polyoxyethylene (8) nonylphenolethin; about 1.3 parts by weight sodium lauryl sulphate; about 40 parts by weight fatty alcohol alkoxylate; about 8 parts by weight plant terpenes; about 667 parts by weight of diammonium phosphate in three parts by weight water. In an alternate embodiment, diammonium phosphate was replaced with an alternative nitrogen-containing nutrient such as ammonium sulphate or ammonium nitrate.

EXAMPLE 6

Control of Winter Wheat Using a Sprayable and Bioactive Mixture of Formulation Aid with Glyphosate Technical Acid and Ammonium Sulphate in Comparison to Roundup Transorb.

Table 7 shows the use of formulation aid with glyphosate technical acid 95% with or without ammonium sulphate in comparison to Roundup Transorb, a pre-formulated herbicide, for controlling winter wheat. Percent control 7, 14, 28 & 56 days after treatment (DAT) of winter wheat was recorded. Plots (2×10 meter) were applied in the summer of 2000 using a precision plot sprayer at 200 l/ha Formulation aid and glyphosate technical acid 95% alone was less effective in controlling winter wheat than Roundup Transorb or formulation aid with ammonium sulphate at 7, 14, 28 DAT. However, formulation aid and glyphosate technical acid 95% alone were equally effective in controlling winter wheat than Roundup Transorb or formulation aid with ammonium sulphate at 56 DAT.

The agrochemical formulation aid tested in this example with glyphosate technical acid contained about 150 parts by weight mineral oil paraffinic distillate; about 26 parts by weight 2N-octanol; about 47.2 parts by weight oleyl-cetyl alcohol; about 50.2 parts by weight polyoxyethylene (2) oleylether; about 50 parts by weight polyoxyethylene (8) nonylphenolethin; about 1 part by weight sodium lauryl sulphate; about 39.4 parts by weight fatty alcohol alkoxylate; about 8.6 parts by weight plant terpenes; about 667 parts by weight of diammonium phosphate in three parts by weight water. In an alternate embodiment, diammonium phosphate was replaced with an alternative nitrogen-containing nutrient such as ammonium sulphate or ammonium nitrate.

EXAMPLE 7

Post Emergent Broadleaf Weed Control Using Formulation Aid with Dicamba Technical Acid in Comparison to Banvel 11

Table 8 shows post emergent broadleaf weed control using the formulation aid with dicamba technical acid 87% in comparison to Banvel 11, a pre-formulated dicamba herbicide. The mixture was applied to 5-leaf stage corn in 2×10 meter plots with a precision plot sprayer at 200 l/ha in the summer of 2000. Percent weed control 28 days after treatment (DAT) was recorded. Formulation aid and dicamba technical acid 87% were more effective than Banvel 11 at both treatment rates. In another experiment, the formulation aid was used in combination with Prosulfuron, another pre-formulated herbicide and dicamba technical acid. Percentage control was as good as when Prosulfuron and Banvel 11 were used with a commercial adjuvant, Agral 90.

The agrochemical formulation aid tested in this example contained about 150 parts by weight mineral oil paraffinic distillate; about 26 parts by weight 2N-octanol; about 47.2 parts by weight oleyl-cetyl alcohol; about 50.2 parts by weight polyoxyethylene (2) oleylether; about 50 parts by weight polyoxyethylene (8) nonylphenolethin; about 1 part by weight sodium lauryl sulphate; about 39.4 parts by weight fatty alcohol alkoxylate; about 8.6 parts by weight plant terpenes; about 667 parts by weight of diammonium phosphate in three parts by weight water. In an alternate embodiment, diammonium phosphate was replaced with an alternative nitrogen-containing nutrient such as ammonium sulphate or ammonium nitrate.

EXAMPLE 8

Broadleaf Weed Control in Turf Grass Using the Formulation Aid with 2,4-D Technical Acid or Dicamba Technical Acid Alone and in Combination in Comparison to Commercial Formulations This example demonstrates the use of formulation aid of the present invention in rendering 2,4-D technical acid, dicamba technical acid, and a combination thereof into an agriculturally and horticulturally acceptable form. This preparation is bioactive and spray-applicable at lower vapor pressure and has no odor problems.

Table 9 shows broadleaf weed control in Turf grass using the formulation aid with 2,4-D 96% technical acid or dicamba 98% technical acid alone and in combination in comparison to commercial formulations of 2,4-D and dicamba i.e., 2,4-D amine and Banvel 11. Treatments were applied using a precision plot sprayer at 200 l/ha to 2×8 meter plots during the fall of 2000. Percentage of injury on crop and percentage control of weeds was recorded 30 days after treatment.

The agrochemical formulation aid tested in this example contained about 150 parts by weight mineral oil paraffinic distillate; about 26 parts by weight 2N-octanol; about 47 parts by weight oleyl-cetyl alcohol; about 51 parts by weight polyoxyethylene(2)oleylether; about 10 parts by weight polyoxyethylene(8) nonylphenolethin; about 1 part by weight sodium lauryl sulphate; about 39 parts by weight fatty alcohol alkoxylate; about 8 parts by weight plant terpenes; about 667 parts by weight of diammonium phosphate in three parts by weight water; about 2.5% weight by volume of tetrasodium ethylene diamine tetracetate; and from about 10 to 20 parts by weight of cab-o-sil. In an alternate embodiment, diammonium phosphate was replaced with an alternative nitrogen-containing nutrient such as ammonium sulphate or ammonium nitrate.

EXAMPLE 9

Fall Control of Alfalfa Using the Formulation Aid with Glyph Sate Technical Acid and 2,4-D Technical Acid or Glyphosate Technical Acid and Dicamba Technical Acid in Comparison to Pre-formulated Products This example demonstrates the use of formulation aid of the present invention in rendering the combination of glyphosate technical acid and 2,4-D technical acid or glyphosate technical acid and dicamba technical acid into an agriculturally or horticulturally acceptable form that is bioactive and spray applicable.

Table 10 shows fall control of Alfalfa using the formulation aid with glyphosate technical acid 95% and 2,4-D technical acid 96% or glyphosate technical acid 95% and dicamba technical acid 98% in comparison to pre-formulated products. Plots (2×8 meter) were sprayed with a precision plot sprayer at 200 l/ha in the fall, 2000 by Agriculture Canada, Harrow, Ontario, Canada. In comparison to use of pre-formulated products, the use of technical acids with the formulation aid of the present invention caused less injury to the crop.

The agrochemical formulation aid tested in this example contained about 150 parts by weight mineral oil paraffinic distillate; about 26 parts by weight 2N-octanol; about 47 parts by weight oleyl-cetyl alcohol; about 50 parts by weight polyoxyethylene (2) oleylether; about 10 parts by weight polyoxyethylene (8) nonylphenolethin; about 1 part by weight sodium lauryl sulphate; about 39 parts by weight fatty alcohol alkoxylate; about 8 parts by weight plant terpenes; about 5 parts by weight methyl alcohol; about 667 parts by weight of diammonium phosphate in three parts by weight water; and about 2 parts weight by volume of tetrasodium ethylene diamine tetracetate; and from about 10 to 20 parts by weight of cab-o-sil. In an alternate embodiment, diammonium phosphate was replaced with an alternative nitrogen-containing nutrient such as ammonium sulphate or ammonium nitrate.

EXAMPLE 10

Effectiveness of the Formulation Aid with Glyph Sate Technical Acid or Pre-formulated Agrochemical Pesticides Under Controlled Greenhouse Conditions This example demonstrates the use of formulation aid of the present invention in rendering glyphosate technical acid, manufacturing concentrates or pre-formulated agrochemical pesticides into an agriculturally or horticulturally acceptable form that is bioactive and spray applicable.

Table 11, 12, 13 and 14 show effectiveness of the formulation aid with glyphosate technical acid or pre-formulated agrochemical pesticides in controlled greenhouse conditions during summer of 2001 in controlling several weeds such as Velvetleaf, Barnyard grass, and Lambsquarters. Herbicides, technical acid with the formulation aid or formulated products, were applied at 0.25 lb ae/h. The formulation aid was used at 0.3% v/v. AMS was used at 1% or 8.5 lb/100 gallon of water. The mixture was sprayed at 20 gallons per acre at 30 pounds per square inch of pressure. The results indicate that the formulation aid works with formulated products also. The formulated products may contain different adjuvants. The results also indicate that the addition of AMS improved effectiveness of herbicides in controlling weeds.

The agrochemical formulation aid tested in this example contained about 6.7% by weight of mineral oil paraffinic distillate; about 14.9% by weight of aromatic hydrocarbon distillate; about 5.7% by weight of ATPLUS 300 F; about 2.2% by weight of 2N-octanol; about 3.9% by weight of oleyl-cetyl alcohol; about 33.3% by weight of polyoxyalkylated fatty alcohol; and about 33.3% by weight of ethoxylated tallow amine blend.

EXAMPLE 11

Effectiveness of the Water Conditioning Formulation Aid with Technical Acid or Pre-formulated Agrochemical Pesticides Under Controlled Greenhouse Conditions and Field Conditions.

This example demonstrates the use of the water conditioning formulation aid of the present invention in rendering glyphosate technical acid, manufacturing concentrates or pre-formulated agrochemical pesticides into an agriculturally acceptable form that is bioactive and spray applicable.

Tables 15 and 16 show effectiveness of the water conditioning formulation aid with glyphosate technical acid or pre-formulated agrochemical pesticides in controlled greenhouse and field conditions during the Summer and Fall of 2002.

The weed species controlled were Velvetleaf, Lambsquarters and Giant Foxtail in greenhouse research and ratings were taken on Alfalfa, Common Chickweed and Dandelion in field trials.

The Formulated herbicides were compared to technical acid glyphosate. All herbicide treatments were applied with the novel water conditioning formulation aid, diammonium sulphate or without a water conditioner. Rate of glyphosate used was 228 grams ae/ha in greenhouse trials conducted at Michigan State University in June of 2002. The rate of glyphosate in Trials at the University of Guelph was 450 gm ae/Ha.

The formulation aid—water conditioner tested in this example contained 85% by weight monocarbamide dihydrogen sulphate with 15% by weight of an adjuvant blend (AX-0127B) comprised of 31% phosphate ester blend; 21.5% by weight tallow amine ethoxylate, 20.7% methyl soyate, 7.2% polyethylene glycol, 5.8% linear alcohol blend, 1.9% tall oil fatty acid, 0.9% by weight butanol and 11% water called N Tank A.

Another variation in the formulation called N Tank B was comprised of 85% by weight monocarbamide dihydrogen sulphate and 15% by weight of a blend of phosphate esters and tallow amine ethoxylate (AX-0306) and tested at Michigan State University on Velvetleaf and Giant Foxtail (Table 17). Results of this trial indicate excellent performance when used with a glyphosate acid as well as with formulated glyphosates.

The commercial names and the suppliers of the components used in formulation aids are:

mineral oil paraffinic distillate: Sun Cropspray 11N, Sunoco Inc., Ten Penn Center, 1801 Market Street, Philadelphia, Pa. 19103;

aromatic hydrocarbon distillate: SOLVESSO 200, Imperial Oil, Products and Chemicals Division, 111 St. Clair Avenue West PO Box 4029 Stn A, Toronto, Ontario, Canada;

surfactant blend: ATPLUS 300 F, Uniqema, 1000 Uniqema Boulevard, New Castle, Del., USA;

2N-octanol: Jarchem Industries Inc., 414 Wilson Avenue, Newark, N.J., USA;

oleyl-cetyl alcohol: HD Ocenol 80/85, Cognis Corporation, 5051 Estecreek Drive, Cincinnati, Ohio, USA;

polyoxylkylated fatty alcohol: KLEARFAC AA270 surfactant, BASF Corporation 3000 Continental Drive North, Mount Olive, N.J., USA; and ethoxylated tallow amine blend: HENKEL 6821 A, Agnique GPU Booster 6821A, Cognis Corporation, 5051 Estecreek Drive, Cincinnati, Ohio, USA.

polyoxyethylene (2) oleylether: Brij 93, ICI Americas Inc., Wilmington, Del.

polyoxyethylene (8) nonylphenolethin::Renex 688, ICI Americas Inc, Wilmington, Del., USA;

Fatty alcohol alkoxylate: Plurafac LF 700, BASF Canada Inc., Toronto, Ontario Canada;

plant terpenes: Orange Terpenes, Gerard-Roure Inc., Brampton, Ontario, Canada Monocarbamide dihydrogen sulfate: N-pHURIC, Agrium Inc. 13131 Lake Fraser Drive SE, Calgary, Alberta.

Phosphate ester blend and tallow amine ethoxylate (AX-0306) and a complex blend (AX-0127B): Adjuvants Unlimited Inc. 3633 Charles Page Blvd, Tulsa Okla.

Other components are routinely available.

The above-described embodiments of the invention are intended to be examples of the present invention. Alterations, modifications and variations may be effected to the particular embodiments by those of skill in the art, without departing from the scope of the invention which is defined solely by the claims appended hereto.

TABLE 1

Amounts of glyphosate technical acid (N-phosphonomethylglycine, 95–99.9%) active ingredient or product and formulation aid required to prepare a sprayable and bioactive mixture.

| Component A | | Component B | |
|---|---|---|---|
| Glyphosate technical acid (95%) (Kg ae*)/hectare | Glyphosate technical grade (95%) (Kg product)/hectare | Formulation aid per 100 to 150 liters/ha water volume | Formulation aid per 50 liters/ha water volume |
| 0.225 | 0.24 | 0.5 | 0.5 |
| 0.500 | 0.53 | 0.5 | 1.1 |
| 0.675 | 0.7 | 0.9 | 1.6 |
| 0.9 | 0.94 | 1.1 | 2.3 |
| 1.5 | 1.6 | 1.9 | 2.3 |
| 2.0 | 2.1 | 2.5 | 2.3 |

*Active ingredient

TABLE 2

Control of broad-spectrum weeds by using formulation aid of the present invention with non-formulated herbicide, glyphosate technical acid, at various application rates.

| Glyphosate + formulation aid* | Canada Thistle | Lambs-quarters | Quack-grass** | Annual grasses*** | Dandelions | Sow Thistle | Pig Weed | Catnip |
|---|---|---|---|---|---|---|---|---|
| 0.94 + 0.9 | 100% | 100% | 100% | 100% | 100% | 100% | 100% | 100% |
| 0.7 + 0.7 | 100% | 100% | 100% | 100% | 100% | 100% | 100% | 100% |
| 0.53 + 0.5 | 100% | 100% | 100% | 100% | 100% | 100% | 100% | 100% |
| 0.24 + 0.5 | 80% | 80% | 80% | 90% | 80% | 90% | 100% | 80% |
| 0.94 + water | 0% | 0% | 0% | 0% | 0% | 0% | 0% | 0% |
| 0.53 + water | 0% | 0% | 0% | 0% | 0% | 0% | 0% | 0% |
| 0.24 + water | 0% | 0% | 0% | 0% | 0% | 0% | 0% | 0% |

*Glyphosate technical acid (95%) (Kg or l)/ha + formulation aid (l)/ha
**Includes other perennial grasses such as wirestem muhly
***Annual grasses included foxtails, annual bluegrass, crabgrass, witchgrass

TABLE 3

Control of broad-spectrum weeds by using formulation aid of the present invention with non-formulated herbicide, Dicamba technical acid, at various application rates.

| Dicamba + formulation aid* | Canada Thistle | Lambs-quarters | Quack Grass** | Various annual grasses*** | Dandelions | Sow Thistle | Pig Weed | Catnip |
|---|---|---|---|---|---|---|---|---|
| 0.140 + 1.0 | N/A | 100% | N/A | N/A | N/A | N/A | 100% | N/A |
| 0.280 + 1.0 | N/A | 100% | N/A | N/A | N/A | N/A | 100% | N/A |
| 0.140 + water | N/A | 0% | N/A | N/A | N/A | N/A | 0% | N/A |
| 0.280 + water | N/A | 0% | N/A | N/A | N/A | N/A | 0% | N/A |

Dicamba 95% (Kg) + formulation aid (L)/ha
*includes other perennial grasses such as wirestem muhly
***various annual grasses including foxtails, annual bluegrass, crabgrass, witch grass
N/A: Not applicable

TABLE 4

Amounts of Dicamba technical acid (3,6-dichloro-2-methoxybenozic acid, 88–95%) and formulation aid required to prepare a sprayable and bioactive mixture for spraying.

| Component A Dicamba technical acid (88–95%) (Kg)/hectare | Component B Formulation aid (l)/water volume |
|---|---|
| 0.140 | 0.5% v/v |
| 0.280 | 0.5% v/v |

TABLE 5

Control of weeds using a mixture of glyphosate technical acid or glyphosate wet cake isopropyl amine technical acid and the formulation aid and Roundup Transorb.

| Treatments | Rate | Redroot Pigweed | Lambs quarters | Green Foxtail | Smooth Crabgrass |
|---|---|---|---|---|---|
| | | | % Control | | |
| Glyphosate 95% ta* + Formulation aid | 225 gm ae**/ha 1.5% v/v | 81.3% | 63.8% | 83.8% | 67.5% |
| Glyphosate 97% wc*** + Formulation aid | 225 gm ae/ha 1.5% v/v | 83.8% | 78.8% | 83.8% | 61.3% |
| Roundup Transorb | 225 gm ae/ha | 68.5% | 61.3% | 81.6% | 73.5% |

*technical acid
**active ingredient
***wet cake isopropyl amine technical acid.

TABLE 6

Control of pre-plant vegetation using a sprayable and bioactive mixture of glyphosate technical acid and the formulation aid.

| Treatments | Rates | Giant Foxtail | Yellow oxtail | Velvet leaf | Smart weed |
|---|---|---|---|---|---|
| Roundup Ultra | 450 gm ae*/ha | 100 | 98 | 85 | 30 |
| Glyphosate ta** + Formulation aid | 450 gm ae/ha 450 ml/ha | 100 | 90 | 82 | 65 |
| Glyphosate ta + Formulation aid + AMS*** | 450 gm ae/ha 450 ml/ha 1% v/v | 100 | 95 | 93 | 85 |

*Active ingredient
**Technical acid
***Ammonium sulphate

TABLE 7

Control of winter wheat using a mixture of formulation aid with glyphosate technical acid with and without ammonium sulphate in comparison to Roundup Transorb, a pre-formulated herbicide.

| | | % Control | | | |
|---|---|---|---|---|---|
| Treatments | Rates | 7 DAT | 14 DAT | 28 DAT | 56 DAT |
| Roundup Transorb | 450 gm ae/ha | 15 c | 23 c | 53 b | 100 a |
| Glyphosate ta** + Formulation aid | 450 gm ae/ha 450 ml/ha | 4 de | 6 e | 20 d | 100 a |

TABLE 7-continued

Control of winter wheat using a mixture of formulation aid with glyphosate technical acid with and without ammonium sulphate in comparison to Roundup Transorb, a pre-formulated herbicide.

| Treatments | Rates | 7 DAT | 14 DAT | 28 DAT | 56 DAT |
|---|---|---|---|---|---|
| Glyphosate ta + Formulation aid + AMS*** | 450 gm ae/ha 450 ml/ha 1% v/v | 20 b | 29 b | 83 a | 100 a |

Means followed by the same letter do not significantly differ (P = .05, LSD)
*Active ingredient
**Technical acid
**Ammonium sulphate

TABLE 8

Post emergent broadleaf weed control using the formulation aid with dicamba technical acid 87% in comparison to Banvel 11, a pre-formulated dicamba herbicide.

| Treatment | Rate | Velvet Leaf | Lambs Quarters | Redroot Pigweed |
|---|---|---|---|---|
| | | | % Control | |
| Banvel 11 | 70 g ae*/ha | 23 d | 18 e | 18 c |
| Dicamba tech** + Formulation aid | 70 g ae/ha 0.5% v/v | 36 bc | 63 c | 43 b |
| Banvel 11 | 140 g ae/ha | 35 cd | 35 d | 58 b |
| Dicamba tech + Formulation aid | 140 g ae/ha 0.5% v/v | 49 b | 79 b | 58 b |
| Prosulfuron + Banvel 11 + Agral 90 | 10 g ae/ha 140 g ae/ha 0.2% v/v | 98 a | 93 a | 97 a |
| Prosulfuron + Dicamba tech + Formulation aid | 10 g ae/ha 140 g ae/ha 0.5% v/v | 99 a | 96 a | 98 a |

Means followed by the same letter do not significantly differ (P = .05, LSD).
*active ingredient
**dicamba technical acid

TABLE 9

Control of broadleaf weeds in Turfgrass using the formulation aid with 2,4-D technical acid or dicamba technical acid alone or in combination in comparison to commercial, formulations of 2,4-D or dicamba.

| Treatment | Rate | % Crop Injury | Dandelion | Chickweed | White clover |
|---|---|---|---|---|---|
| | | | | % Control | |
| 2,4-D amine | 0.7 k ae*/ha | 0.0 c | 56.7 bc | 56.7 a | 53.3 b |
| 2,4-D 96% ta** + Formulation aid | 0.7 k ae/ha 0.5% v/v | 0.0 c | 50.0 bc | 63.7 a | 70.0 ab |
| Banvel 11 | 0.6 k ae/ha | 0.0 c | 71.7 abc | 100.0 a | 100.0 a |
| Dicamba 98% ta + Formulation aid | 0.6 k ae/ha 1.0% v/v | 15 a | 88.3 a | 100.0 a | 100.0 a |
| 2,4-D amine | 1.4 k ae/ha | 6.7 b | 63.3 abc | 83.3 a | 100.0 a |
| 2,4-D 96% ta + Formulation aid | 1.4 k ae/ha 1.0% v/v | 0.0 c | 70.0 abc | 90.0 a | 83.3 ab |
| 2,4-D amine + Banvel 11 | 0.7 k ae/ha 0.07 k ae/ha | 0.0 c | 70.0 abc | 100.0 a | 70.0 ab |
| 2,4-D 96% ta + dicamba 98% ta + Formulation aid | 0.7 k ae/ha 0.07 k ae/ha 0.5% v/v | 0.0 c | 41.7 c | 73.3 a | 93.3 a |
| 2,4-D amine + Banvel 11 | 1.4 k ae/ha | 0.0 c | 78.3 ab | 100.0 a | 100.0 a |
| 2,4-D 96% ta + dicamba 98% ta + formulation aid | 1.4 k ae/ha 0.14 k ae/ha 1.0% v/v | 0.0 c | 68.3 abc | 73.3 a | 100.0 a |

Means followed by the same letter do not significantly differ (P = .05, Duncan's New MRT).
*Active ingredient
**Technical acid

TABLE 10

Control of Alfalfa using the formulation aid with glyphosate technical acid and 2,4-D technical acid or glyphosate technical acid and dicamba technical acid in comparison to pre-formulated products.

| Treatments | Rates | % injury | % control |
|---|---|---|---|
| Roundup Transorb 2,4-D amine | 0.5 kg ae*/ha 0.5 kg ae/ha | 71.3 ab | 100 |
| Glyphosate 95% ta** + 2,4-D 96% ta + formulation aid | 0.5 kg ae/ha 0.5 kg ae/ha 0.5% v/v | 47.5 cd | 100 |
| Roundup Transorb + 2,4-D amine | 1.0 kg ae/ha 1.0 kg ae/ha | 77.5 a | 100 |
| Glyphosate 95% ta + 2,4-D 96% ta + formulation aid | 1.0 kg ae/ha 1.0 kg ae/ha 1.0% v/v | 75.0 ab | 100 |
| Roundup Transorb + Banvel 11 | 0.5 kg ae/ha 0.5 kg ae/ha | 73.8 ab | 100 |
| Glyphosate 95% ta + Dicamba 98% ta + Formulation aid | 0.5 kg ae/ha 0.5 kg ae/ha 0.5% v/v | 47.5 cd | 100 |
| Roundup Transorb + Banvel 11 | 1.0 kg ae/ha 1.0 kg ae/ha | 75.0 ab | 100 |
| Glyphosate 95% ta + Dicamba 98% ta + Formulation aid | 1.0 kg ae/ha 1.0 kg ae/ha 1.0% v/v | 77.5 a | 100 |

Means followed by the same letter do not significantly differ (P = .05, Duncan's New MRT).
*Active ingredient
**Technical acid

TABLE 11

Control of Velvetleaf using the formulation aid with glyphosate technical acid or formulated agrochemical pesticides in controlled greenhouse conditions.

| TRT NO. | Treatment | 7 DAT | 10 DAT | 14 DAT |
|---|---|---|---|---|
| | | | % Control | |
| 1 | Control | 0 G | 0 E | 0 E |
| 2 | Glyfos* | 13 g | 10 e | 23 d |
| 3 | Glyfos + formulation aid | 12 g | 10 e | 15 d e |
| 4 | Glyfos + formulation aid + AMS | 40 e f | 43 d | 70 a b c |
| 5 | Glyphomax** | 52 b c d e | 60 c d | 67 a b c |
| 6 | Glyphomax + formulation aid | 43 d e f | 77 a b c | 81 a b c |
| 7 | Glyphomax + formulation aid + AMS | 38 e f | 78 a b c | 82 a b c |
| 8 | RoundUp UltraMax*** | 10 g | 13 e | 7 d e |

TABLE 11-continued

Control of Velvetleaf using the formulation aid with glyphosate technical acid or formulated agrochemical pesticides in controlled greenhouse conditions.

| TRT NO. | Treatment | % Control 7 DAT | 10 DAT | 14 DAT |
|---|---|---|---|---|
| 9 | RoundUp UltraMax + AMS | 60 a b c | 70 a b c | 78 a b c |
|  | LSD (0.05) | 16 | 19 | 23 |

Means followed by the same letter do not significantly differ (P = .05, Duncan's New MRT).
*glyphosate amine (IPA salt)
**glyphosate amine (IPA salt)
***glyphosate amine (IPA salt)

TABLE 12

Control of barnyard grass using the formulation aid with glyphosate technical acid or formulated agrochemical pesticides in controlled greenhouse conditions.

| TRT NO. | Treatment | % Control 7 DAT | 10 DAT | 14 DAT |
|---|---|---|---|---|
| 1 | Control | 0 h | 0 k | 0 h |
| 2 | Glyfos* | 38 e f | 40 h i j | 30 g |
| 3 | Glyphomax** | 55 b c d | 36 i j | 40 e f |
| 4 | Glyfos + formulation aid | 53 c d | 48 f g h | 48 e |
| 5 | Glyphomax + formulation aid | 28 f g | 45 g h i | 34 f g |
| 6 | Glyfos + formulation aid + AMS | 63 a b c | 64 b c d | 70 a b |
| 7 | Glyphomax + formulation aid + AMS | 55 b c d | 66 a b c | 73 a b |
| 8 | Glyphosate ta* + formulation aid + AMS | 71 a | 74 a | 69 b c |
| 9 | RoundUp UltraMax*** | 18 g | 33 j | 0 h |
| 10 | RoundUp UltraMax + AMS | 66 a b | 68 a b c | 69 b c |
|  | LSD (0.05) | 13 | 10 | 10 |

Means followed by the same letter do not significantly differ (P = .05, Duncan's New MRT).
*glyphosate amine (IPA salt)
**glyphosate amine (IPA salt)
***glyphosate amine (IPA salt)

TABLE 13

Control of Velvetleaf using the formulation aid with glyphosate technical acid or formulated agrochemical pesticides in controlled greenhouse conditions.

| TRT NO. | Treatment | % Control 7 DAT | 10 DAT | 14 DAT |
|---|---|---|---|---|
| 1 | Control | 0 i | 0 j | 0 e |
| 2 | Glyfos* | 13 g h | 13 i | 13 d e |
| 3 | Glyfos + formulation aid | 45 f | 49 h | 53 c |
| 4 | Glyfos + formulation aid + AMS | 65 a b c d e | 68 c d e f | 65 a b c |
| 5 | Glyphomax** | 23 g | 15 i | 15 d |
| 6 | Glyphomax + formulation aid | 63 b c d e | 50 g h | 53 c |
| 7 | Glyphomax + formulation aid + AMS | 70 a b c | 71 a b c d e | 70 a b |
| 8 | Glyphosate ta + formulation aid + AMS | 60 c d e | 63 e f | 63 b c |
| 9 | RoundUp UltraMax*** | 10 h i | 14 i | 18 d |
| 10 | RoundUp UltraMax + AMS | 60 c d e | 66 d e f | 68 a b |
|  | LSD (0.05) | 11 | 11 | 13 |

Means followed by the same letter do not significantly differ (P = .05, Duncan's New MRT).
*glyphosate amine (IPA salt)
**glyphosate amine (IPA salt)
***glyphosate amine (IPA salt)

TABLE 14

Control of Lambsquarters using the formulation aid with glyphosate technical acid or formulated agrochemical pesticides in controlled greenhouse conditions.

| TRT NO. | Treatment | % Control 7 DAT | 10 DAT | 14 DAT |
|---|---|---|---|---|
| 1 | Control | 1 g h | 0 j | 0 i |
| 2 | Glyfos* | 9 f g h | 1 j | 0 i |
| 3 | Glyfos + formulation aid | 9 f g h | 10 h i j | 0 i |
| 4 | Glyfos + formulation aid + AMS | 23 b c d | 30 b c d e | 18 e f g h |
| 5 | Glyphomax** | 11 e f g | 15 g h i | 5 h i |
| 6 | Glyphomax + formulation aid | 18 c d e f | 25 c d e f g | 15 f g h |
| 7 | Glyphomax + formulation aid + AMS | 16 c d e f | 20 e f g h | 33 a b c d |
| 8 | Glyphosate ta + formulation aid + AMS | 40 a | 40 a b | 44 a |
| 9 | RoundUp UltraMax*** | 3 g h | 0 j | 0 i |
| 10 | RoundUp UltraMax + AMS | 33 a b | 33 a b c d | 36 a b c |
|  | LSD (0.05) | 11 | 11 | 15 |

Means followed by the same letter do not significantly differ (P = .05, Duncan's New MRT).
*glyphosate amine (IPA salt)
**glyphosate amine (IPA salt)
***glyphosate amine (IPA salt)

TABLE 15

A comparison of various products for Velvetleaf and Giant Foxtail control at 0.26 kg ae/ha and Lambsquarters control at 0.4 kg ae/ha of glyphosate. The Greenhouse trials were conducted at Michigan State University and applied at 10 gpa and 25 psi.

| Trt | Treatment | Velvetleaf % Injury 14 DAT | Lambsquarters % Injury 14 DAT | Giant Foxtail % Injury 14 DAT |
|---|---|---|---|---|
| 1 | Control | 0 g | 0 g | 0 g |
| 2 | Glyfos* | 29 ef | 51 f | 62 de |
| 3 | Glyfos + 2% AMS** | 82 ab | 59 def | 100 a |
| 4 | Glyfos + 1% N Tank | 79 ab | 72 abc | 100 a |
| 5 | Glyphomax* | 28 ef | 66 bcde | 60 de |
| 6 | Glyphomax + 2% AMS | 75 abc | 62 cdef | 100 a |
| 7 | Glyphomax + 1% N Tank A | 77 abc | 69 abcde | 99 a |
| 8 | Glyphosate Acid*** | 19 f | 6 g | 39 f |
| 9 | Glyphosate Acid + 2% AMS | 73 abc | 4 g | 70 cd |
| 10 | Glyphosate Acid + 1% N Tank A | 75 abc | 58 ef | 91 ab |
| 11 | Roundup WeatherMax**** | 37 ef | 52 f | 55 e |
| 12 | Roundup WeatherMax + 2% AMS | 73 abc | 77 ab | 96 a |
| 13 | Roundup WeatherMax + 1% N TankA | 76 abc | 78 ab | 100 a |
| 14 | Roundup UltraMax* | 37 ef | 74 ab | 78 bc |
| 15 | Roundup UltraMax + 2% AMS | 83 a | 70 abcd | 100 a |
| 16 | Roundup UltraMax + 1% N Tank A | 79 ab | 70 abcd | 98 a |
| | LSD (0.05) | 15 | 14 | 13 |

*Glyphosate IPA salt
**AMS is diammonium Sulphate
***Glyphosate acid
****Glyphosate potassium salt

TABLE 16

Alfalfa, Chickweed and Dandelion control with Fall applied herbicides in field trials conducted at the University of Guelph, Ridgetown. All glyphosate treatments were applied at 450 grams ae/ha or ½ liter per acre in 20 gallons of spray solution.

| Trt | Treatment | Alfalfa 29 DAT | Chickweed 29 DAT | Dandelion 29 DAT |
|---|---|---|---|---|
| 1 | Control | 0 g | 0 c | 0 d |
| 2 | ClearOut 41* | 58 f | 90 ab | 83 c |
| 3 | ClearOut 41 + Reddy IT** 0.3% v/v + AMS*** 1% wt/v | 88 ab | 86 ab | 90 ab |
| 4 | ClearOut 41 + N Tank A 1.5% v/v | 91 ab | 93 ab | 90 ab |
| 5 | ClearOut 41 Plus* | 75 de | 89 ab | 88 abc |
| 6 | ClearOut 41 Plus + Reddy IT 0.3% v/v + AMS 1% wt/v | 85 bc | 89 ab | 91 ab |
| 7 | ClearOut 41 Plus + N Tank A 1% v/v | 90 ab | 94 ab | 90 ab |
| 8 | ClearOut Tec Acid 96.7% | 68 e | 83 b | 87 bc |
| 9 | ClearOut Tec Acid 96.7% + Reddy IT 0.3% v/v + AMS 1% wt/v | 85 bc | 91 ab | 91 ab |
| 10 | ClearOut Tec Acid 96.7% + N Tank A 1.5% v/v | 91 ab | 95 a | 94 a |
| 11 | Roundup Transorb* | 80 cd | 93 ab | 88 abc |
| 12 | Roundup Transorb + Reddy IT 0.3% v/v + AMS 1% wt/v | 90 ab | 86 ab | 90 ab |
| 13 | Roundup Transorb + N Tank A 1% v/v | 88 abc | 86 ab | 90 ab |
| 14 | Touchdown IQ* | 75 de | 90 ab | 88 abc |
| 15 | Touchdown IQ + Reddy IT 0.3% v/v + AMS 1% wt/v | 88 abc | 85 ab | 86 bc |
| 16 | Touchdown IQ + N Tank A 1% v/v | 94 a | 89 ab | 94 a |
| 17 | Reddy IT 0.3% v/v | 0 g | 0 c | 0 d |
| 18 | N Tank A 1.5% v/v | 0 g | 0 c | 0 d |
| | LSD (P = 0.05) | 8.2 | 11 | 6 |
| | Standard Deviation | 5.8 | 7.9 | 5 |
| | CV | 8.4 | 11 | 6 |

*Glyphosate IPA salt
**Reddy IT adjuvant
***Diammonium sulfate

The formulation aid—water conditioners tested in this example contained 85% by weight monocarbamide dihydrogen sulphate with 15% by weight of an adjuvant blend comprised of 33.3% phosphate ester blend; 66.7% by weight tallow amine ethoxylate and is called N Tank B as well as 85% by weight monocarbamide dihydrogen sulphate with 15% by weight of an adjuvant blend comprised of 66.7% phosphate ester blend; 33.3% by weight tallow amine ethoxylate and is called N Tank B are compared to previously described N Tank A.

TABLE 17

Michigan State University Greenhouse Trials Spring 2003 on Velvetleaf and Giant Foxtail Performance of N Tank B and N Tank C are compared with N Tank A with glyphosate acid, ClearOut 41, ClearOut 41 Plus and Roundup Weathermax.

| TRT NO. | TREATMENTS | Velvetleaf % CONTROL 14 DAT | | Giant Foxtail % CONTROL 14 DAT | |
|---|---|---|---|---|---|
| 1 | CONTROL | 6 | de | 0 | j |
| 2 | GLYPHOSATE ACID 96.7%* | 5 | de | 15 | i |
| 3 | GLYPHOSATE ACID + 2% AMS** | 72 | b | 53 | h |
| 4 | GLYPHOSATE ACID + 1% N TANK A | 83 | ab | 59 | gh |
| 5 | GLYPHOSATE ACID + 1% N TANK B | 84 | a | 89 | abcd |
| 6 | GLYPHOSATE ACID + 1% N TANK C | 86 | a | 69 | fg |
| 7 | CLEAROUT 41* | 14 | d | 53 | h |
| 8 | CLEAROUT 41 + 2% AMS | 78 | ab | 60 | gh |
| 9 | CLEAROUT 41 + 1% N TANK A | 81 | ab | 74 | ef |
| 10 | CLEAROUT 41 + 1% N TANK B | 84 | a | 95 | ab |
| 11 | CLEAROUT 41 + 1% N TANK C | 87 | a | 90 | abcd |
| 12 | CLEAROUT 41 PLUS* | 32 | c | 84 | bcde |
| 13 | CLEAROUT 41 PLUS + 2% AMS | 83 | a | 94 | abc |
| 14 | CLEAROUT 41 PLUS + 1% N TANK A | 83 | a | 81 | de |
| 15 | CLEAROUT 41 PLUS + 1% N TANK B | 87 | a | 96 | ab |
| 16 | CLEAROUT 41 PLUS + 1% N TANK C | 83 | ab | 96 | ab |
| 17 | ROUNDUP WEATHERMAX*** | 3 | e | 62 | fgh |
| 18 | ROUNDUP WEATHERMAX + 2% AMS | 78 | ab | 92 | abcd |
| 20 | ROUNDUP WEATHERMAX + 1% N TANK A | 86 | a | 83 | cde |
| 21 | ROUNDUP WEATHERMAX + 1% N TANK B | 83 | a | 98 | a |
| 22 | ROUNDUP WEATHERMAX + 1% N TANK C | 81 | ab | 93 | abcd |
| | LSD (0.05) | 6 | | 13 | |

*glyphosate acid
**diammonium sulfate
***glyphosate IPA salt

What is claimed is:

1. An agrochemical formulation aid composition comprising about 1 to 99 parts by weight of monocarbamide dihydrogen sulphate and 50 to 1 parts by weight of a blend, said blend comprising:
    25-75% by weight of a phosphate ester;
    75-25% by weight of a tallow amine ethoxylate;
    3-5% by weight of a fatty acid methyl ester;
    0.1-3% by weight of a free fatty acid;
    0.1-1% by weight of a linear alcohol;
    1-6% by weight of oleyl-cetyl alcohol;
    0.5 to 1.5% by weight of polyethylene glycol; and
    balance, if any, of water.

2. An agrochemical formulation aid composition comprising about 1 to 99 parts by weight of monocarbamide dihydrogen sulphate and 50 to 1 parts by weight of a blend, said blend comprising:
    a phosphate ester;
    a tallow amine ethoxylate;
    20-25% by weight of a fatty acid methyl ester;
    0.1-3% by weight of a free fatty acid;
    3-6% by weight of 2N-octanol;
    5-10% by weight of oleyl-cetyl alcohol;
    0.1-1% by weight of N-butanol;
    7.2% by weight of polyethylene glycol; and
    balance, if any, of water.

3. The agrochemical formulation aid composition of claim 1 wherein said blend comprises:
    about 3-5% by weight of a fatty acid methyl ester;
    about 0.1-3% by weight free fatty acid;
    about 0.5-3% by weight of 2N-octanol;
    about 1-6% by weight of oleyl-cetyl alcohol;
    from about 0.1-1% by weight N-butanol;
    from about 3-10% by weight of alkyl(aryl)ethoxylate phosphate ester as phosphate ester;
    from about 3-12% by weight tallow amine ethoxylate; and
    from about 0.5 to 1.5% by weight polyethylene glycol.

4. An agrochemical formulation aid composition comprising about 85% by weight of monocarbamide dihydrogen sulphate and about 15% by weight of a blend, said blend comprising:
    31% phosphate ester;
    21.5% by weight tallow amine ethoxylate,
    20.7% methyl soyate,
    7.2% polyethylene glycol,
    5.8% linear alcohol,
    1.9% tall oil fatty acid,
    0.9% by weight butanol, and
    11% water.

5. The agrochemical formulation aid composition of claim 1 comprising about 85% by weight of monocarbamide dihydrogen sulphate and about 15% by weight of said blend, said blend comprising about 25 to 75% by weight of alkyl(aryl) ethoxylate phosphate esters as said phosphate ester and about 75 to 25% by weight of said tallow amine ethoxylate.

* * * * *